United States Patent [19]

Neumann

[11] Patent Number: 5,476,003
[45] Date of Patent: Dec. 19, 1995

[54] MEASURING SENSOR FOR DETERMINING GAS COMPOSITIONS

[75] Inventor: Harald Neumann, Vaihingen, Germany

[73] Assignee: Robert Bosch GmbH, Stuttgart, Germany

[21] Appl. No.: 294,014

[22] Filed: Aug. 23, 1994

[30] Foreign Application Priority Data

Oct. 5, 1993 [DE] Germany ............................ 43 33 898.4

[51] Int. Cl.⁶ .......................... G01N 27/407; H01C 7/115
[52] U.S. Cl. .............................. 73/31.06; 338/34; 422/98
[58] Field of Search ...................... 73/31.06; 340/634; 338/34; 422/98

[56] References Cited

U.S. PATENT DOCUMENTS

| | | | |
|---|---|---|---|
| 3,695,848 | 10/1972 | Taguchi | 73/31.06 |
| 3,872,419 | 3/1975 | Groves et al. | 340/628 |
| 4,355,056 | 10/1982 | Dalla Betta et al. | 338/34 |
| 4,786,476 | 11/1988 | Munakata et al. | 422/98 |
| 4,931,851 | 6/1990 | Sibbald et al. | 73/31.06 |
| 5,296,836 | 3/1994 | Saburi et al. | 338/34 |
| 5,334,350 | 8/1994 | Friese et al. | 73/31.06 |
| 5,367,283 | 11/1994 | Lauf et al. | 338/34 |

FOREIGN PATENT DOCUMENTS

| | | | |
|---|---|---|---|
| 140340 | 5/1985 | European Pat. Off. | |
| 2923816 | 12/1979 | Germany. | |
| 2908916 | 9/1980 | Germany. | |
| 118656 | 9/1981 | Japan | 338/34 |
| 52247 | 2/1990 | Japan | 338/34 |
| 263145 | 10/1990 | Japan | 73/31.06 |
| 344450 | 12/1992 | Japan | 73/31.06 |
| 126777 | 5/1993 | Japan | 73/31.06 |

Primary Examiner—Thomas P. Noland
Assistant Examiner—Daniel S. Larkin
Attorney, Agent, or Firm—Spencer, Frank & Schneider

[57] ABSTRACT

A measuring sensor for determining gas compositions, includes a substrate consisting essentially of $Al_2O_3$, electrodes disposed on the substrate, a sensor layer consisting essentially of $TiO_2$ disposed above the electrodes, and an adhesion-improving layer which consists essentially of $Al_2TiO_5$ and which is disposed on the substrate, the adhesion-improving layer being at least partially connected with the electrodes. The adhesion-improving layer is provided to improve the adhesiveness of the electrodes, and includes a material in common with the material of the sensor layer, i.e., Ti. The material of the adhesion-improving layer is selected so as to prevent a chemical reaction between the materials of the substrate and the sensor layer.

6 Claims, 1 Drawing Sheet

MEASURING SENSOR FOR DETERMINING GAS COMPOSITIONS

CROSS-REFERENCE TO RELATED APPLICATION

This application is related to German application No. DE P 43 33 898.4 filed Oct. 5, 1993 the entire specification of which is incorporated herein by reference.

1. Field of the Invention

The invention provides an improved measuring sensor for determining gas compositions.

2. Technology Review

Resistance measuring sensors are known from, for example, DE 2,908,916 in which electrodes, a semiconductor layer and a gas-permeable cover layer are applied to a ceramic substrate. To improve the adhesion between the semiconductor layer and the substrate, it has been proposed to provide a sintered layer which is permanently sintered with the substrate and extends into the sensor layer, anchoring the sensor layer. In this connection it was also proposed to include an additional, adhesion-improving layer between the sintered layer and the electrodes to improve the adhesion therebetween. The material of the sintered layer and/or the adhesion-improving layer is adapted to the properties of the substrate material.

It is further known from EP-A-140,340 to sprinkle the substrate of a measuring sensor with ceramic particles which bond with the substrate during sintering. The particles permanently bonded to the substrate produce a rough surface as the adhering base for the semiconductor layer above it. This method requires that the ceramic particles cover the entire surface and adhere both to the substrate and the electrode surface. This reduces the contact surface between sensor layer and electrodes, increasing the internal resistance of the resistance measuring sensor.

SUMMARY OF THE INVENTION

The measuring sensor of the invention has the advantage that the adhesion-improving layer can be produced with the screen-printing method, and can therefore be integrated better into the manufacturing process of such multilayer ceramics. At the same time, a sufficient stability is achieved of the layer system under continuous stress. Through the use of materials of the same composition, with reference to the material of the sensor layer, for the adhesion-improving layer, chemical reactions between the substrate and the sensor layer, which are chemically different, are prevented. Chemical reactions are restricted to the boundary surface between substrate and adhesion-improving layer, where they cannot exert an interfering influence on the electrodes. Material of the same composition is to be understood as material which contains at least the principal substance or the compound of the sensor layer material. Also included is a material that results as a reaction product of the materials of the substrate and sensor layer.

Advantageous modifications and improvements of the measuring sensor system are possible. For example, a particularly good adhesion of the electrodes is achieved when the electrodes are made of a cermet material and the sintering activity of the ceramic of the cermet material is adapted to the material of the adhesion-improving layer. The best properties are achieved when the material of the adhesion-improving layer is used as the ceramic of the cermet material. The improvement in adhesion can be further increased by means of making use of pores on the boundary surface of the adhesion-improving layer.

Embodiments of the invention are described in detail in the drawings and in the following description.

DETAILED DESCRIPTION OF THE INVENTION

Figure 1:
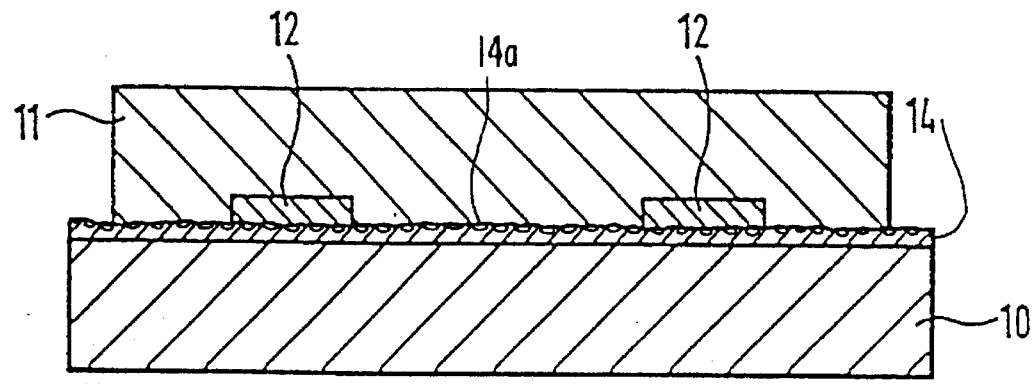
FIG. 1 is a cross-section through the measuring sensor of the invention in a first embodiment

FIG. 1 shows a cross-section through the layer system of a resistance measuring sensor having a substrate 10 of, for example, aluminum oxide containing more than 90% $Al_2O_3$. Substrate 10 can be used in both the pre-sintered or completely-sintered stage. An adhesion-improving layer 14 is applied to the substrate. Two electrodes 12, which extend next to one another, are disposed on adhesion-improving layer 14. A sensor layer 11 of a semiconductive metal oxide, for example titanium oxide, is positioned on top of electrodes 12. The resistance measuring sensor is further typically configured to include a heater, not shown. This heater is of a conventional type and is well known.

In the present embodiment, adhesion-improving layer 14 is made of, for example, the material of sensor layer 11, for example, titanium oxide. Through the use of material of the same composition in reference to sensor layer 11, with the present selection of material, aluminum titanate forms on the boundary surface between adhesion-improving layer 14 and sensor layer 11. If adhesion-improving layer 14 were adapted in its material properties to substrate 10 rather than to sensor layer 11, aluminum titanate would form on the boundary surface between adhesion-improving layer 14 and sensor layer 11. This, however, would lead to impairment of the electrodes. The formation of aluminum titanate progresses over the service life, leading to an ever-increasing impairment of the sensor function. Ultimately, this means that the sensitivity of the resistance measuring sensor decreases over the service life and finally becomes instable.

A further suitable material for adhesion-improving layer 14 is, for example, aluminum titanate ($Al_2TiO_5$). This material results from the chemical reaction between the $Al_2O_3$ substrate and the $TiO_2$ sensor layer.

A further embodiment consists of the addition of a pore-forming material to the printing paste of adhesion-improving layer 14; this material escapes during sintering and thus forms a porous surface 14a on adhesion-improving layer 14. Pore-forming materials are conventional and have long been known.

To produce the resistance measurement sensor, adhesion-improving layer 14 is pressed onto the pre-sintered or completely sintered substrate 10, for example using screen printing technology. Following a drying step, the two electrodes 12 and, possibly, the electrode conductor tracks, not shown, are applied to adhesion-improving layer 14 by means of a printing paste. Subsequently, sensor layer 11 is pressed on top of electrodes 12. Further, a porous protective layer, not shown in the present embodiment, can be disposed above sensor layer 11. The printing steps for electrodes 12, sensor layer 11 and the possibly applied porous protective layer are likewise performed using printing screen technology. The layer system is subsequently sintered at a temperature of 1200° to 1600° C., preferably at 1400° C.

It is, however, also possible not to produce the layer system in a co-sintering process, as described above, but to perform a first sintering after the application of adhesion-improving layer 14 and electrodes 12. Sensor layer 11 is then applied to the adhesion-improving layer 14 after it has been sintered; sensor layer 11 is sintered together with substrate 10 and the sintered, adhesion-improving layer 14 in a second sintering process.

Figure 2:
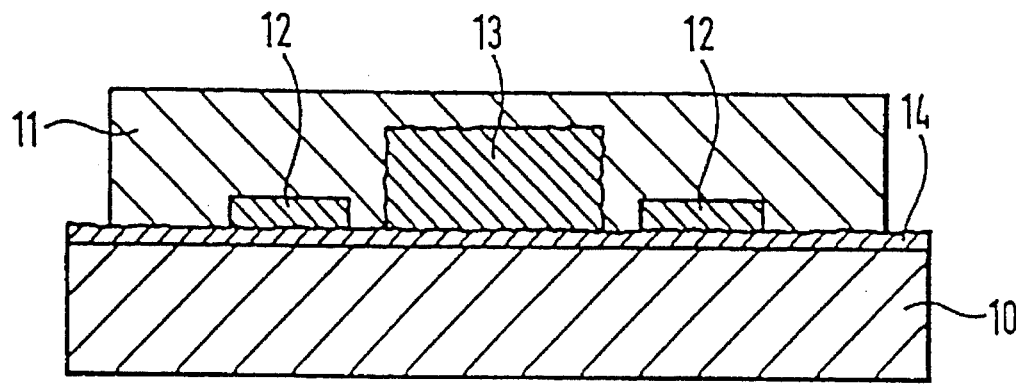
FIG. 2 is a cross-section through the measuring sensor of the invention in a second embodiment.

FIG. 2 shows a second embodiment, in which the individual layers are produced analogously to the above-described embodiment. In addition, in this embodiment a layer section 13 is provided which protrudes into sensor layer 11 for increased adhesion of sensor layer 11 on adhesion-improving layer 14. Layer section 13 serves to further increase the adhesion of sensor layer 11 on adhesion-improving layer 14. Layer section 13 is preferably made of the same material as adhesion-improving layer 14, and can be individually sintered together with adhesion-improving layer 14 or, as already described, co-sintered with the entire layer system.

A further embodiment is possible in which adhesion-improving layer 14 is substantially limited to the region of electrodes 12. Substantially limited to the region of the electrodes is to be understood as at least about 75% by weight of said layer is between said electrodes and said substrate. In doing so, an improvement in adhesion with substrate 10, particularly for electrodes 12, is achieved. For a resistance measuring sensor having high stability, the adhesion of the electrodes is of particular importance. Detachment of the electrodes from substrate 10 would eventually lead to transition resistances which would increase and/or change over an extended service life.

Figure 3:
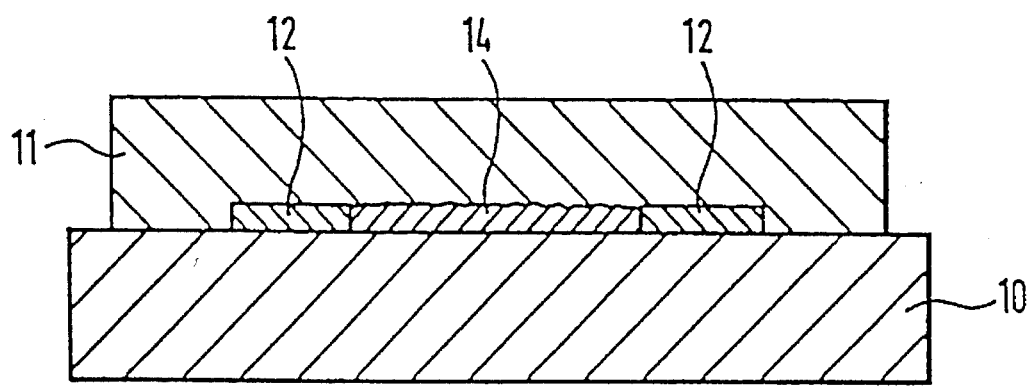
FIG. 3 is a cross-section through the measuring sensor of the invention in a third embodiment..

A third embodiment is based on FIG. 3, in which adhesion-improving layer 14 and electrodes 12 are disposed on substrate 10. At its side surfaces, layer 14 is connected to the side surfaces of electrodes 12. The good adhesion of sensor layer 11 between electrodes 12 is sufficient for a good adhesive connection of the layer system.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A measuring sensor for determining gas compositions, comprising:

a substrate consisting essentially of $Al_2O_3$, electrodes disposed on the substrate, a sensor layer consisting essentially of $TiO_2$ disposed above the electrodes, and an adhesion-improving layer which consists essentially of $Al_2TiO_5$ and which is disposed on the substrate, the adhesion-improving layer being at least partially connected with the electrodes.

2. The measuring sensor as defined in claim 1, wherein the adhesion-improving layer is partially disposed between the electrodes and the substrate.

3. The measuring sensor as defined in claim 1, wherein a layer section which protrudes into the sensor layer disposed above it is provided on the adhesion-improving layer.

4. The measuring sensor as defined in claim 1, wherein the adhesion-improving layer is substantially disposed between the electrodes on the substrate.

5. The measuring sensor as defined in claim 1, wherein the adhesion-improving layer has at least one porous surface.

6. The measuring sensor as defined in claim 1, wherein the electrodes are made of a cermet material, and the ceramic of the cermet material is of the same composition as the material of the adhesion-improving layer.

\* \* \* \* \*